United States Patent
Schönfeld et al.

[11] Patent Number: 5,866,798
[45] Date of Patent: Feb. 2, 1999

[54] CRYSTAL OSCILLATOR SENSOR

[75] Inventors: Axel Schönfeld, Wiesbaden; Gernot Feucht, Mutterstadt; George Frank, Tübingen, all of Germany

[73] Assignee: Hoechst Aktiengesellschaft, Germany

[21] Appl. No.: 627,265

[22] Filed: Apr. 4, 1996

[30] Foreign Application Priority Data

Apr. 5, 1995 [DE] Germany ............... 195 12 739.0

[51] Int. Cl.$^6$ .................................... G01N 11/16
[52] U.S. Cl. .................. 73/24.06; 73/61.49; 422/88; 422/69
[58] Field of Search ............... 73/24.01, 24.06, 73/61.49, 64.53; 422/69, 88

[56] References Cited

U.S. PATENT DOCUMENTS

| | | | |
|---|---|---|---|
| 3,260,104 | 7/1966 | King, Jr. ................... | 73/24.06 |
| 3,778,229 | 12/1973 | Webster et al. . | |
| 3,864,324 | 2/1975 | Yukuta et al. ............ | 260/94.7 |
| 4,243,631 | 1/1981 | Ryerson . | |
| 5,076,094 | 12/1991 | Frye et al. ................ | 73/24.06 |
| 5,185,129 | 2/1993 | Koutrakis et al. . | |

FOREIGN PATENT DOCUMENTS

| | | | |
|---|---|---|---|
| WO91/05998 | 5/1991 | WIPO . | |
| 94/18551 | 8/1994 | WIPO ................... | 73/24.01 |

OTHER PUBLICATIONS

Analytical Chemistry, Band 57, Nr.,3, 1985, H.M. FOG "Piezolectric Crystal Detector for the Monitoring of Ozone in Working Envioments" Seiten 2634–2638.

*Primary Examiner*—Michael Brock
*Attorney, Agent, or Firm*—Connolly & Hutz

[57] ABSTRACT

The crystal oscillator sensor is provided with a coating comprising a polymer having olefinic side groups. The coating polymer used is, for example, substituted polyacrylate, polymethacrylate, polystyrene or polyester. The sensor is suitable for detecting ozone.

7 Claims, No Drawings

CRYSTAL OSCILLATOR SENSOR

The invention describes a sensor based on the piezoelectric effect, with the sensor being coated with an active, mass-responsive layer of polymers containing olefinic side groups, and also its use for detecting ozone.

It is known (Analyt. Chem., 57(13), 2634–8, 1985) that ozone can be detected using a piezoelectric sensor coated with 1,4-polybutadiene. A problem with this process is the production of the polymer coating by means of application with a brush. The surface of the contact can be damaged in this way. Likewise, the homogeneity of the layer cannot be made reproducible by means of this process, which is confirmed by the frequency change range indicated (2 000 to 10 000 Hz). Furthermore, the observed frequency changes caused by exposure to amounts of ozone in the ppb range are so small that they are of the order of magnitude of the noise of the eigenfrequency of the piezoelectric crystal (3 to 30 Hz).

The reaction of the ozone with the 1,4-polybutadiene forms low molecular weight compounds which can partially volatilize. This leads to an opposite mass change and thus to an error in the concentration determination of the gas. Furthermore, low molecular weight compounds, particularly in thin layers, show a strong tendency to crystallize and this generally impairs the ability of the crystal to oscillate.

Polybutadiene generally tends, even at slightly elevated temperatures, to undergo a strong crosslinking reaction, so that such a crystal oscillator sensor quickly ages and becomes unusable even in ozone-free air.

It is also known that electronic frequency generators utilize a piezoelectric element of quartz or PZT ceramic for generating vibrations. One of the resonant frequencies is selected for detecting mass changes and is reinforced by the connected external frequency generator. In the frequency range up to about 20 MHz, the frequency concerned is that of the fundamental vibration which is excited into resonance in this way.

In the case of piezoelectrics, the following function (Sauerbrey equation) applies to the frequency change $\Delta f$:

$$\Delta f = -2.3 * 10^6 * F^2 \Delta m/A$$

where A is the vibrating area, F is the fundamental frequency and $\Delta m$ is the mass change. If a vibrating surface (e.g. a crystal plate) is provided with a coating, the frequency of the sensor system changes because of the increase in mass.

If the coating has absorbing properties in respect of one or more materials in the surrounding medium, the vibrating system reacts with a frequency change to absorption taking place. The properties of the sensor (selectivity, sensitivity, regenerability, cumulative capability) can be set within wide limits by appropriate selection of the absorber.

However, it has to be noted here that the vibrational properties of the piezoelectrics must not be impaired by the coating. Furthermore, the absorber must not react with the materials to be detected to form volatile substances. Rapid reaction with the material to be detected is also necessary for effective use.

The ability of the piezoelectric crystal to oscillate is generally lost if the absorber applied to the piezoelectric crystal is of a crystalline or partially crystalline nature. However, in no case is a prediction possible. Even when using organic substances, it is not generally possible to reliably set the required properties exactly. The selection of the substance to be used is therefore more or less empirical.

It is an object of the invention to circumvent the disadvantages mentioned and to provide simple, reliable methods for producing the piezoelectrics and for detecting ozone.

The invention accordingly provides a sensor comprising a piezoelectric crystal which is provided with a coating comprising a polymer having olefinic side groups.

The application of polymers containing olefinic side groups to piezoelectric crystals using suitable coating and further treatment technology has enabled the disadvantages to be eliminated and the desired properties, e.g. high resolution and selectivity and also good aging resistance, to be obtained, thus making available detectors for the quantitative detection of ozone.

Suitable polymers are those containing olefinic side groups or mixtures thereof. In these compounds, the olefinic double bond reacts with the ozone to form ozonides. The structure of the main chain has no influence here. It is possible, for example, to use substituted polyacrylates, substituted polystyrenes or substituted polyesters. The compounds have to have olefinic double bonds in the side group. When using copolymers, it is generally advantageous for at least 3% of olefinic side groups, preferably at least 15% of olefinic side groups, to be present.

In general, suitable polymers are those having a mean molecular weight of from 2 000 to 2 000 000, preferably from 10 000 to 500 000, in particular from 10 000 to 100 000, determined by GPC.

According to the invention, it is possible to use those crystals of inorganic substances which show the piezoelectric effect.

Preference is given to alkaline earth metal titanates, lead/zirconium titanates and quartzes, in particular barium titanate and quartz in the AT section, in which compounds the piezoelectric properties have a particularly low temperature dependence.

The piezoelectric crystals used generally have a fundamental vibration in a frequency range of from 20 kHz to 100 MHz, preferably from 0.1 MHz to 50 MHz and in particular from 0.1 MHz to 30 MHz.

The polymer or polymer mixture used can be applied on one or both sides of the piezoelectric crystals by means of general coating processes. Preference is here given to coating processes based on polymer or monomer solutions, e.g. spincoating, dipcoating or spray processes. Suitable solvents for these processes are all organic substances which dissolve the respective polymer or monomer in a defined temperature interval, for example chloroform. When using monomer solution, the polymerization can be carried out by general surface polymerization techniques such as laser induction or increasing the temperature.

According to the invention, the further treatment of the applied polymer layer is carried out by drying in commercial drying units in air, under protective gas or under reduced pressure at temperatures of from 0° to 350° C., preferably from 30° to 300° C. and in particular from 50° to 300° C. It is also possible to repeat a plurality of coating and drying steps so as to achieve thicker polymer layers.

The weight per unit area of coating on the piezoelectric crystal used after drying is from 1 ng/cm$^2$ to 1 g/cm$^2$, preferably from 5 ng/cm$^2$ to 10 mg/cm$^2$ and in particular from 10 ng/cm$^2$ to 2 mg/cm$^2$.

For example, a crystal oscillator provided with contacts (fundamental vibration between 0.1 and 30 MHz) is coated with polymer dissolved in a solvent (e.g. chloroform, toluene) by means of dipcoating, spincoating or spray processes. This coating can be carried out on one or both sides of the crystal plate by repeating the coating process one or more times. After coating, the sensor is dried in a customary drying unit in air or under reduced pressure.

After drying, the crystal is checked for ability to oscillate. The mass of the absorber layer can be determined from the above-described Sauerbrey equation.

The sensor thus produced is exposed to the gas to be tested in a flow-through cell having a defined volume flow. The sensor frequency is either evaluated directly or mixed with a stabilized reference frequency and then evaluated (plotting of the frequency or the frequency change against time). The signal change can be converted directly into mass changes by means of subsequent processes and shown on a display.

EXAMPLES

Commercial HC-18U crystals (fundamental frequency: 11.5 MHz) were desoldered from their protective casing and dipped into a 1% strength chloroform solution of a polymer of the formula (I)

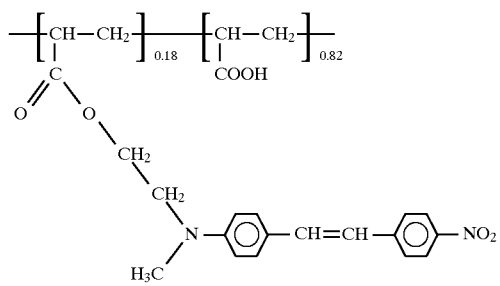

Subsequently, the sensors were dried at 70° C. for 5 hours under reduced pressure. The ability of the coated sensors to oscillate was tested using a transistorized oscillator which allows crystal oscillators to oscillate at between 0.1 and 30 MHz in parallel resonance and a 10 MHz frequency counter (resolution: 0.1 Hz) with connectable upstream divider and thermostatted gate time base.

Sensor 1:
Amount of (I) applied: 3.78 mg
$O_3$ concentration: 1 ppm
Flow rate: ⁻100 1/h

| Time (h) | 0 | 4.5 | 5 | 5.5 | 6 | 6.5 | 7 | 7.5 | 8 | 8.5 | 9 | 9.5 | 10 | 10.5 | 11 | 11.5 | 12 | 12. | 13 | 15 |
|---|---|---|---|---|---|---|---|---|---|---|---|---|---|---|---|---|---|---|---|---|
| Δf [hz] | 0 | 136 | 144 | 156 | 168 | 176 | 184 | 196 | 200 | 208 | 216 | 224 | 236 | 240 | 248 | 252 | 260 | 264 | 276 | 296 |

Sensor 2:
Amount of (I) applied: 3.89 mg
$O_3$ concentration: 1 ppm
Flow rate: ⁻100 1/h

| Time (h) | 0 | 5 | 10 | 15 | 22 | 26 | 32 | 40.4 | 42.4 | 47.4 | 50.4 | 52.4 | 57.4 | 60.4 | 62.4 | 65.4 | 70.4 | 72.4 | 80.4 | 84.4 |
|---|---|---|---|---|---|---|---|---|---|---|---|---|---|---|---|---|---|---|---|---|
| Δf [hz] | 0 | 156 | 212 | 260 | 312 | 354 | 394 | 464 | 480 | 532 | 562 | 580 | 632 | 666 | 686 | 710 | 758 | 776 | 832 | 860 |

The examples show that ozone can be detected almost linearly by means of a sensor comprising polymers having olefinic side groups.

We claim:

1. A sensor comprising a piezoelectric crystal having olefinic side groups, and wherein the polymer having olefinic side groups is selected from the group consisting of a substituted polyacrylate, polymethacrylate, polystyrene and polyester.

2. A sensor as claimed in claim 1, wherein the polymer having olefinic side groups is a copolymer containing at least 3% olefinic side groups.

3. A sensor as claimed in claim 1, wherein the polymer has a mean molecular weight in the range from 2 000 to 10 000 000 g/mol.

4. A sensor as claimed in of claim 1, wherein the piezoelectric crystal has a fundamental vibration in a frequency range of from 20 kHz to 100 MHz.

5. A sensor as claimed in claim 1, wherein the piezoelectric crystal has a harmonic vibration or a surface acoustic wave vibration in the frequency range from 20 kHz to 1000 MHz.

6. A sensor as claimed in claim 1, wherein the piezoelectric crystal used is selected from the group consisting of an alkaline earth metal titanate, lead zirconate titanate and quartz.

7. A sensor comprising a piezoelectric crystal having a coating comprising a polymer having olefinic side groups, and wherein the polymer having olefinic side groups is a polymer of the formula (I)

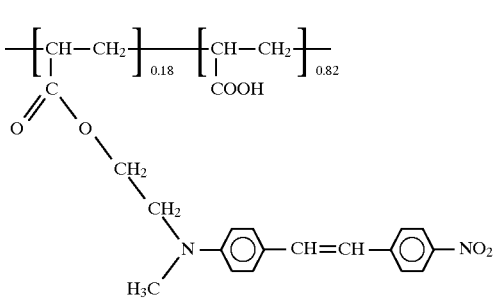

* * * * *

UNITED STATES PATENT AND TRADEMARK OFFICE
CERTIFICATE OF CORRECTION

PATENT NO. : 5,866,798
DATED : February 2,199
INVENTOR(S) : Axel Schonfeld et al.

It is certified that error appears in the above-identified patent and that said Letters Patent is hereby corrected as shown below:

Column 1, line 46, "Am" should read -- Δm --.

Column 3, in table "Time(h)" (first occurrence) "12" (second occurrence) should read -- 12.5 --.

Signed and Sealed this

Twentieth Day of July, 1999

*Attest:*

Q. TODD DICKINSON

*Attesting Officer*    Acting Commissioner of Patents and Trademarks